United States Patent
Lin et al.

(10) Patent No.: US 12,285,594 B2
(45) Date of Patent: Apr. 29, 2025

(54) SYRINGE FOR DETECTING PRESSURE CHANGE

(71) Applicant: FLATTECH, LLC., Taipei (TW)

(72) Inventors: Li-Yu Lin, Taipei (TW); Wen-Fu Luo, Taipei (TW)

(*) Notice: Subject to any disclaimer, the term of this patent is extended or adjusted under 35 U.S.C. 154(b) by 806 days.

(21) Appl. No.: 17/605,000

(22) PCT Filed: Apr. 21, 2020

(86) PCT No.: PCT/US2020/029040
§ 371 (c)(1),
(2) Date: Oct. 20, 2021

(87) PCT Pub. No.: WO2020/219404
PCT Pub. Date: Oct. 29, 2020

(65) Prior Publication Data
US 2022/0203036 A1 Jun. 30, 2022

Related U.S. Application Data

(60) Provisional application No. 62/873,991, filed on Jul. 15, 2019, provisional application No. 62/836,733, filed on Apr. 22, 2019.

(51) Int. Cl.
*A61M 5/315* (2006.01)
*A61M 5/31* (2006.01)

(52) U.S. Cl.
CPC ...... *A61M 5/31505* (2013.01); *A61M 5/3148* (2013.01); *A61M 2005/3128* (2013.01); *A61M 2205/3331* (2013.01)

(58) Field of Classification Search
CPC ............ A61M 5/31505; A61M 5/3148; A61M 2005/3128; A61M 2205/3331
See application file for complete search history.

(56) References Cited

U.S. PATENT DOCUMENTS 4,710,172 A * 12/1987 Jacklich ................ A61M 5/486
604/209
5,159,933 A * 11/1992 Hut .................... A61B 10/0283
600/566

(Continued)

FOREIGN PATENT DOCUMENTS

WO WO2018/208367 A 11/2018

*Primary Examiner* — Manuel A Mendez
(74) *Attorney, Agent, or Firm* — OPES IP Consulting Co., Ltd.

(57) ABSTRACT

The invention provides a syringe for detecting pressure change. The syringe includes a barrel defining a reservoir for receiving a constituent, a piston movable within the reservoir and a plunger. The barrel further includes a proximal end and a distal end with an outlet, an engaging member with a pair of fingers formed on an outer periphery of the barrel and a rib extending from the outer periphery of the barrel and disposed proximally to the engaging member. The plunger includes a first plunger part, a second plunger part and a baseplate supporting the first and second plunger parts. The first plunger part is partially received by the reservoir and slidably engaged with the piston. The second plunger part further includes at least one stop ledge to which the fingers of the engaging member releasably latch, and the stop ledge formed on a periphery of the second plunger part, and a compartment for accommodating a first biasing member with first and second ends. The first and second ends of the first biasing member engage with the rib and the baseplate respectively.

20 Claims, 12 Drawing Sheets

(56) References Cited

U.S. PATENT DOCUMENTS

| | | |
|---|---|---|
| 2010/0179488 A1 | 7/2010 | Spiegel et al. |
| 2014/0288408 A1* | 9/2014 | Deutsch .............. A61M 16/044 128/207.14 |
| 2016/0213854 A1 | 7/2016 | Schwab et al. |

* cited by examiner

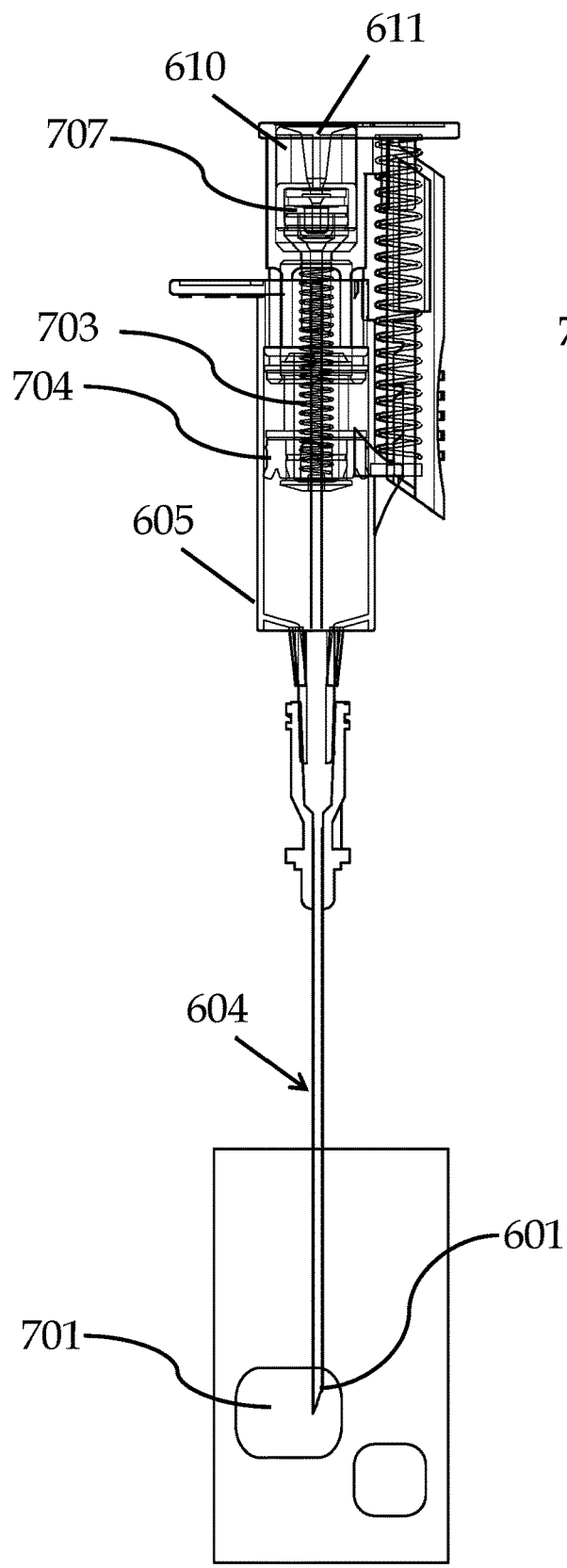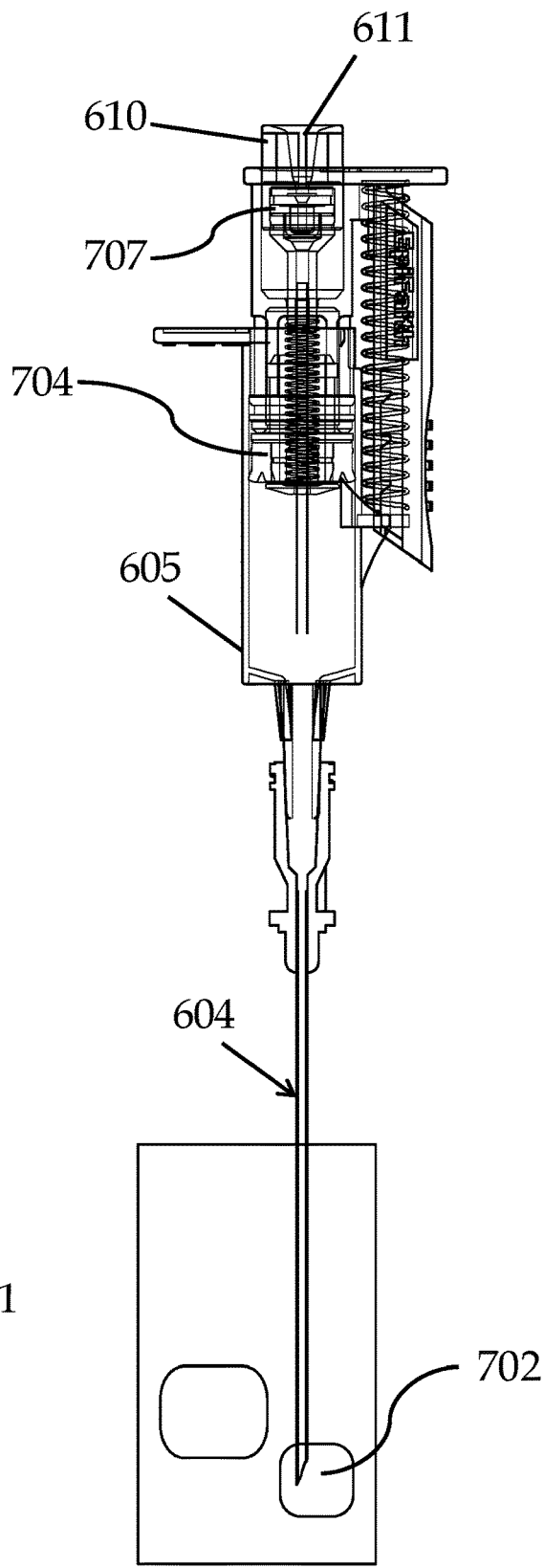
FIG. 7a
FIG. 7b

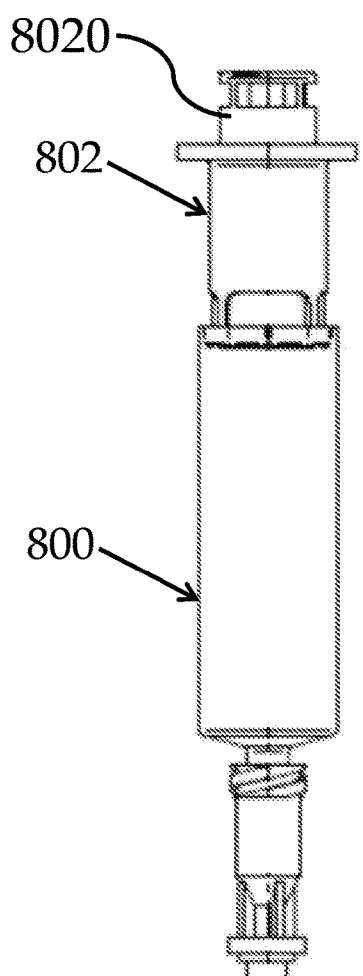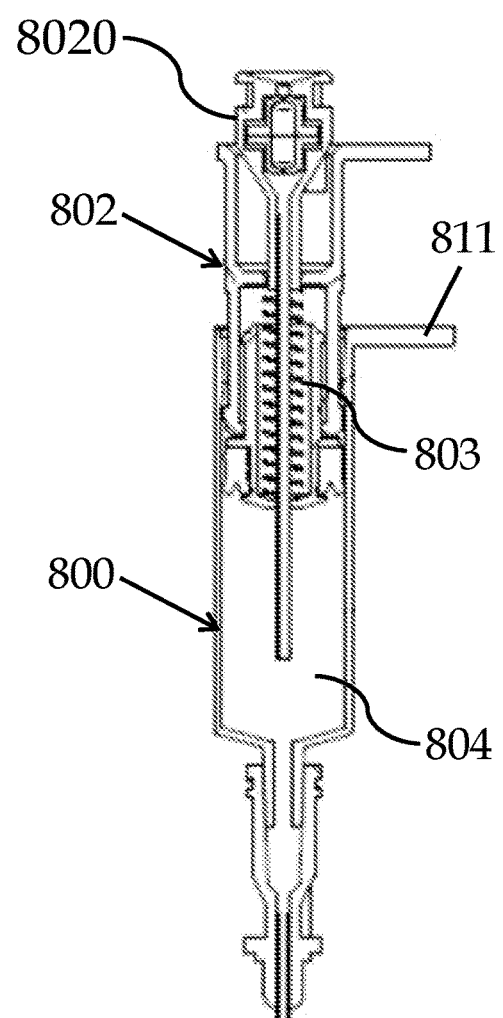
FIG. 8b
FIG. 8c

90

SYRINGE FOR DETECTING PRESSURE CHANGE

CROSS REFERENCE TO RELATED APPLICATION

The present application claims priority to U.S. Provisional Application Ser. No. 62/836,733, filed on Apr. 22, 2019, and to U.S. Provisional Application Ser. No. 62/873,991, filed on Jul. 15, 2019, which are hereby incorporated by reference in their entirety.

FIELD

This invention relates to a syringe, and more particularly, to a syringe capable of detecting a pressure change and further capable of identifying vessel type.

BACKGROUND

Lots of vascular access procedures are carried out by Seldinger technique, for the purposes of placing of needles, guide wires and catheters into vessels for different kinds of indications. Taking central venous catheterization (CVC) as an example, this is a procedure in which a physician localizes a central vein with a needle connected to a syringe or a guide-wire placement device, and the main point of this procedure is to distinguish the artery from vein to avoid large bore puncture of the artery.

However, current techniques require the physician to distinguish the artery by blood color or connecting another tube to see the flow pulsation, which are subjective and carries less precisions. Further, about 0.8% of the artery puncture cannot be identified during central venous catheterization. Even worse, current practices may increase the risks of infection and air embolism.

Many techniques have been proposed to address the issues. For example, U.S. Pat. No. 5,045,065 to Raulerson teaches a catheter introduction syringe and method for the introduction of a catheter or catheter wire into a patient's body. The syringe includes a hollow syringe barrel having a plunger slidably disposed therein. The catheter introduction syringe is capable of functioning as a standard air tight syringe as well as a device to introduce a guidewire. However, the device is unable to differentiate penetration of vessel types.

Compared to aforementioned techniques, measuring the invasive blood pressure is a precious way to distinguish the artery from vein. In peripheral veins used for IV access the average blood pressure is 4 to 8 mmHg. with 7.1 mmHg of mean. The central vein pressure is even lower. The mean central vein pressure is only 4.1 mmHg. On the other hand, in normotensive patients (blood pressure 140/90) the mean blood pressure is 106 mmHg. The arterial pressure is much higher than vein pressure even if the patient has a condition such as heart failure. Please refers to the Table "Blood pressure levels in different portions of the circulatory system in Gayton A. C., Textbook of medical physiology, Philadelphia, 1991, W B Saunders.

Some other techniques were developed accordingly as well. As in U.S. Pat. No. 6,217,558 B1 to Zadini, Zadini teaches a device that enabling the operator to differentiate between blood vessel types by detecting the invasive blood pressure. Moreover, the device can automatically provide a negative pressure within the barrel for auto aspiration when the needle tip arrives at a blood vessel.

However, since the negative pressure mechanism is established within the barrel and the aspirating spring and pressure detecting spring are co-axial placed, the barrel should be made rather long. Moreover, an indicator to easily indicate the measured blood pressure is still missing.

SUMMARY OF THE DISCLOSURE

One of the purposes of the present invention is to provide a syringe that is capable of detecting pressure change.

Another purpose of the present invention is to provide a syringe that is capable of recognizing the types of blood vessels by detecting the invasive blood pressure.

To achieve the foregoing purposes, the syringe for detecting pressure change as provided in the present invention includes a barrel defining a reservoir for receiving a constituent, a piston movable within the reservoir and a plunger. The barrel further includes a proximal end and a distal end with an outlet, an engaging member with a pair of fingers formed on an outer periphery of the barrel and a rib extending from the outer periphery of the barrel and disposed proximally to the engaging member. The plunger includes a first plunger part, a second plunger part and a baseplate supporting the first and second plunger parts. The first plunger part is partially received by the reservoir and slidably engaged with the piston. The second plunger part further includes at least one stop ledge to which the fingers of the engaging member releasably latch, and the stop ledge formed on a periphery of the second plunger part, and a compartment for accommodating a first biasing member with first and second ends. The first and second ends of the first biasing member engage with the rib and the baseplate respectively.

Preferably, when the fingers of the engaging member and the stop ledge are not engaged, the first biasing element is in a normal state, and when the relative position of the plunger and the barrel changes, the first biasing element is compressed.

Preferably, the first biasing element is at a first stage when the first and second engaging elements are engaged, and the first biasing element is at a second stage when the first and second engaging elements are disengaged.

Preferably, a restoring force of the first stage is greater than a restoring force of the second stage.

Preferably, the barrel has a first pressure inside the reservoir when the first biasing element is at the first stage, the first pressure changes to a second pressure in response to the second stage of the first biasing element resulting from the first and second engaging elements are disengaged when the puncturing apparatus connecting to the outlet reaches a first location of a mass.

Preferably, the piston is at a first position relative to the plunger when the second biasing element is at a first state, and the piston maintains in the first position in response to a first pressure change inside the reservoir when the tip of the puncturing apparatus reaches a first location of a mass.

Preferably, the piston is at a first position relative to the plunger when the second biasing element is at a first state, and the piston moves from the first position to a second position in response to a second state of the second biasing element resulting from a first pressure change inside the reservoir when the tip of the puncturing apparatus reaches a first location of a mass, and the piston's change of position is visually detectable.

Preferably, the piston moves from the first position to a third position in response to a third state of the second biasing element resulting from a second pressure change inside the reservoir when the tip of the puncturing apparatus reaches a second location of the mass, and the piston's change of position is visually detectable.

Preferably, a distance from the first position to the third position is longer than a distance from the first position to the second position.

Preferably, the second pressure change is higher than the first pressure change.

To achieve the foregoing purposes, the syringe for detecting pressure change as provided in the present invention includes a barrel defining a reservoir for receiving a constituent and including a proximal end and a distal end with an outlet, a piston movable within the reservoir, a plunger movably within the reservoir and slidably engaged with the piston, and a biasing element disposed between the piston and the plunger. The plunger includes an indicator connecting with the piston, and the indicator further includes an inlet and outlet deposited at a proximal and distal end respectively, a channel connecting the inlet and outlet, and a valve.

Preferably, the syringe further includes a puncturing apparatus having a tip detachably connected to the distal end of the barrel.

Preferably, the indicator is at a first position relative to the plunger when the biasing element is at a first state, and the indicator maintains in the first position in response to a first pressure change inside the reservoir when the tip of the puncturing apparatus reaches a first location of a mass.

Preferably, the indicator does not protrude from an end of the plunger when the tip of the puncturing apparatus reaches the first location of a mass.

Preferably, the indicator is at a first position relative to the plunger when the biasing element is at a first state, and the indicator moves from the first position to a second position in response to a second state of the biasing element resulting from a first pressure change inside the reservoir when the tip of the puncturing apparatus reaches a first location of a mass.

Preferably, the indicator moves from the first position to a third position in response to a third state of the biasing element resulting from a second pressure change inside the reservoir when the tip of the puncturing apparatus reaches a second location of the mass, and the indicator's change of position is visually detectable.

Preferably, a portion of the indicator protrudes from an end of the plunger when the tip of the puncturing apparatus reaches the second location of the mass.

Preferably, the second pressure change is higher than the first pressure change.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed. Certain parts of the drawings are exaggerated for explanation purposes and shall not be considered limiting unless otherwise specified.

FIGS. 7a and 7b are schematic views illustrating how the syringe according to one of the embodiments of the present invention is used;

FIGS. 8a-8c are schematic views illustrating a syringe according to one of the embodiments of the present invention.

Figure 1:
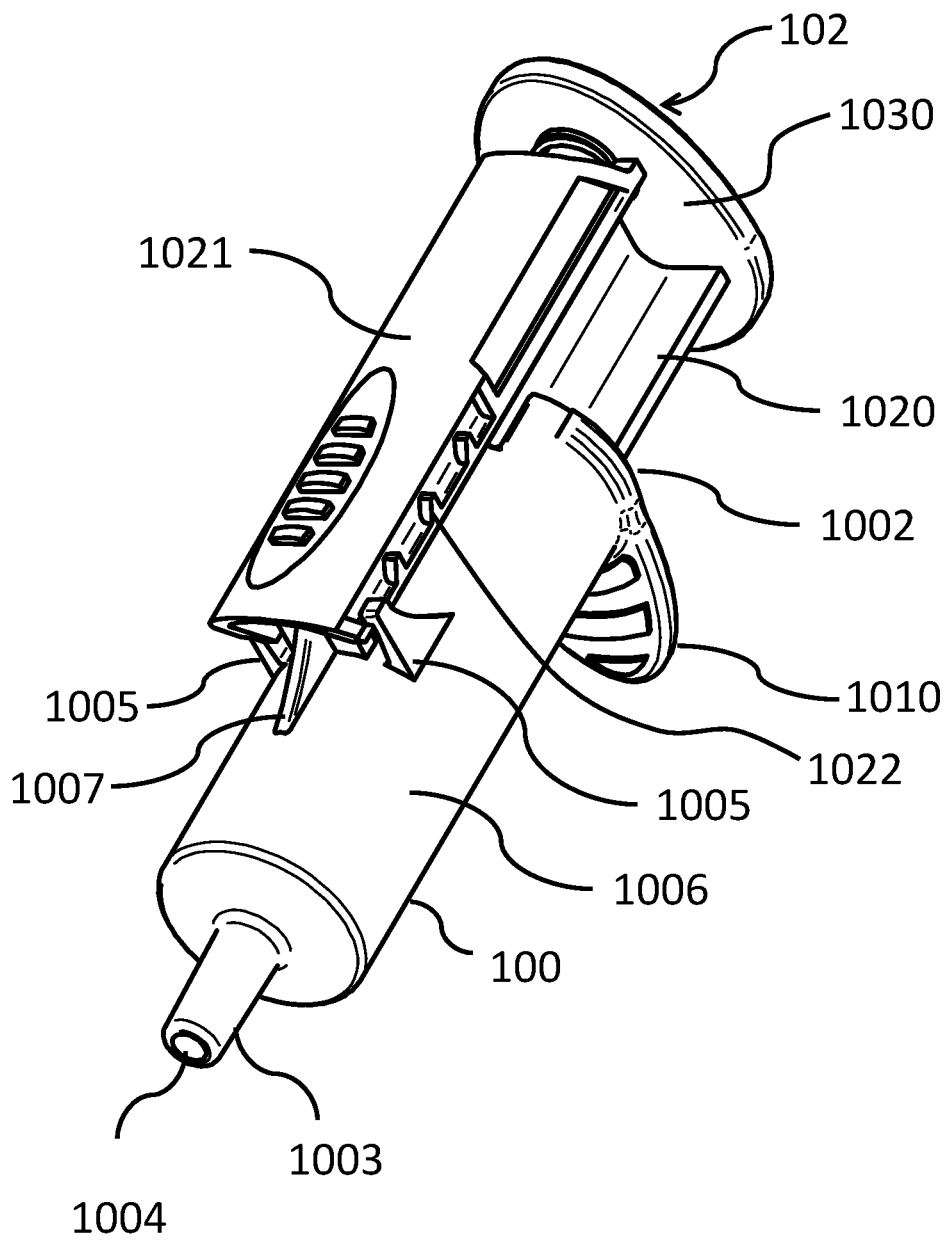
FIG. 1 is a schematic view illustrating a syringe for detecting pressure change according to a first embodiment of the present invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION

Unless defined otherwise, all technical and scientific terms used herein have the same meanings as commonly understood by one of skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2A:
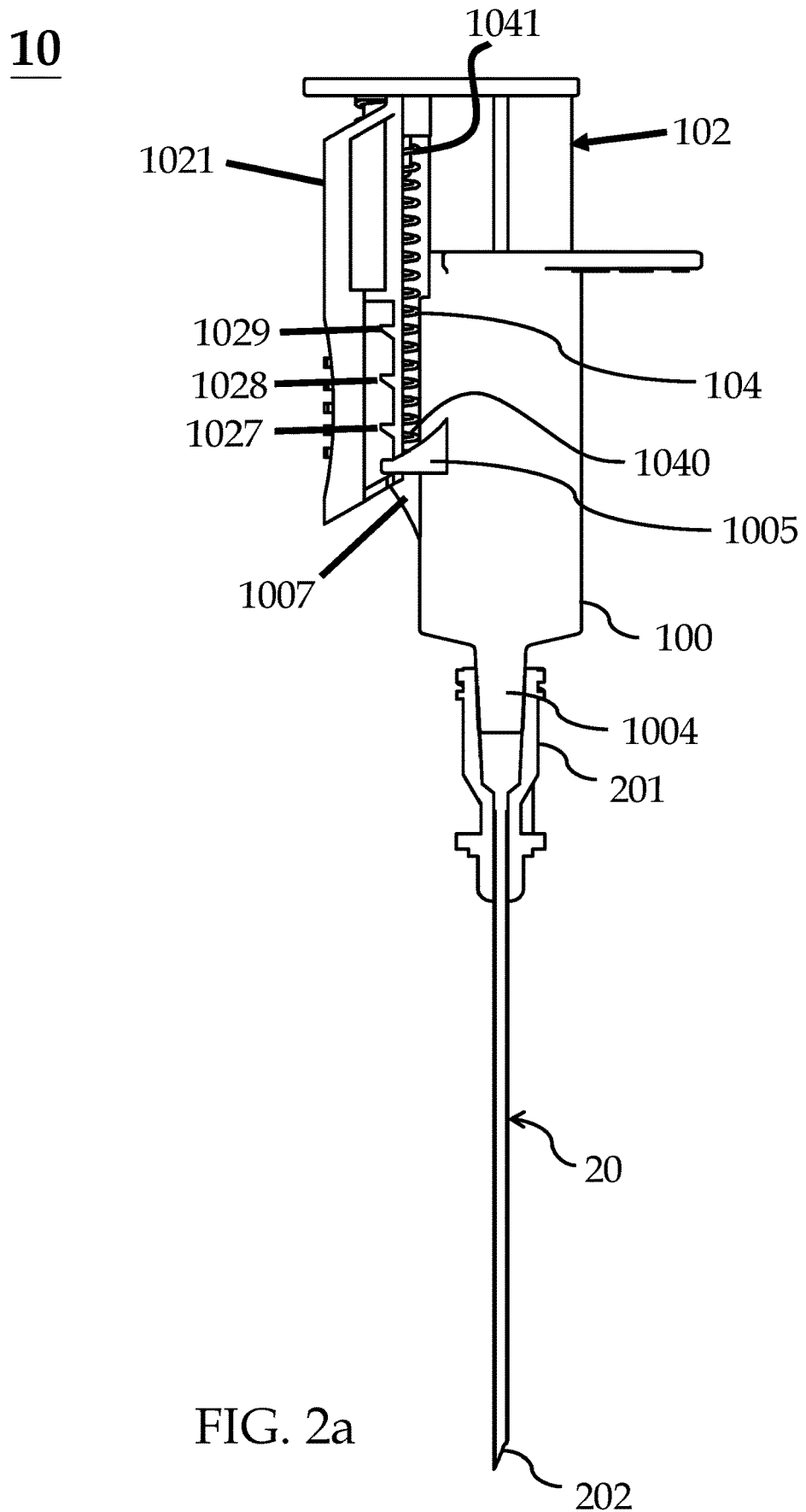
FIGS. 2a and 2b are a side view illustrating a syringe for detecting pressure change according to a first embodiment of the present invention.
Figure 2B:
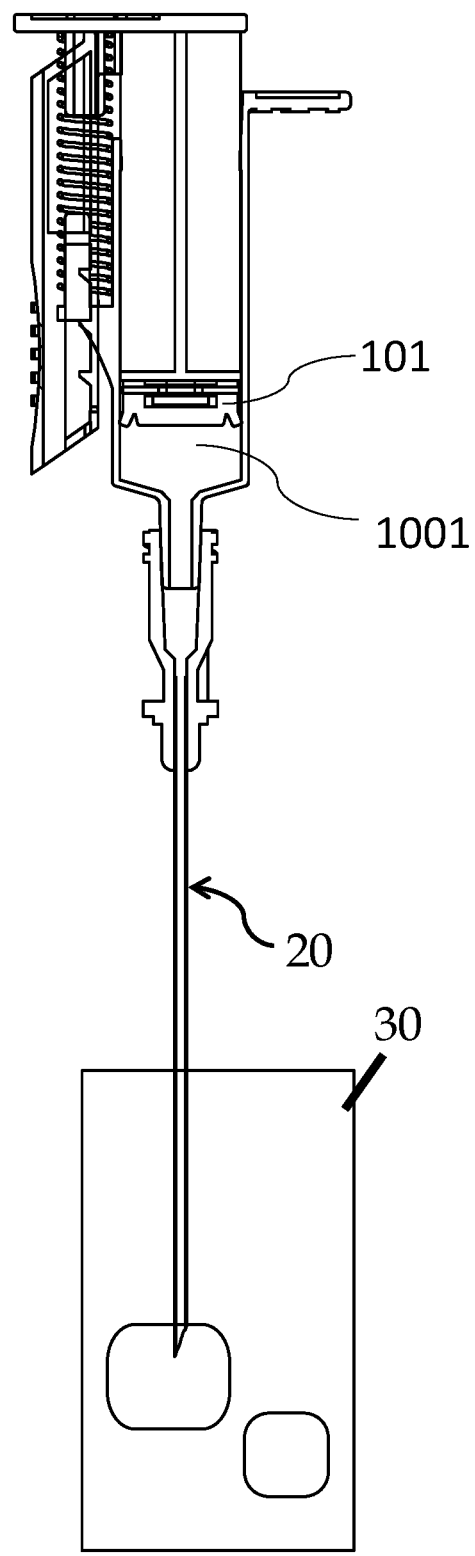

Reference is collectively made to FIGS. 1 and 2a-2b, where FIG. 1 is a schematic view illustrating a syringe for detecting pressure change according to a first embodiment of the present invention, and FIGS. 2a and 2b are a side view illustrating a syringe for detecting pressure change according to a first embodiment of the present invention. As shown in FIGS. 1 and 2a-2b, the syringe 10 of the present invention is capable of detecting pressure change. The syringe 10 includes a barrel 100 defining a reservoir 1001 for receiving a constituent, a piston 101 (not shown in FIGS. 1 and 2a, but can be found in FIG. 2b) movable within the reservoir 1001, and a plunger 102. The constituent may be, blood, air, or physiological saline. The reservoir 1001 is not limited to receive above-mentioned constituents only, but may receive other.

The barrel 100 includes a proximal end 1002 and a distal end 1003 with an outlet 1004, an engaging member 1005 with a pair of fingers 1005 formed on an outer periphery 1006 of the barrel 100, and a rib 1007 extending from the outer periphery 1006 of the barrel 100 and disposed proximally to the engaging member 1005. The piston 101 is movable within the reservoir 1001.

The plunger 102 includes a first plunger part 1020, a second plunger part 1021 and a baseplate 1030. Further, the first plunger part 1020 and the second plunger part 1021 are extending from the baseplate 1030 in the same direction. The first plunger part 1020 partially received by the barrel 100 and slidably engaged with the piston 101, and the first plunger part 1020 is slidable along a longitudinal axis of the barrel 100. The first and second parts 1020, 1021 are supported by the baseplate 1030. In the present embodiment, the first plunger part 1020 and the second plunger part 1021 are substantially in parallel.

The second plunger part 1021 includes at least one stop ledge 1022 to which the fingers 1005 releasably latch, and the at least one stop ledge 1022 is formed on a periphery of the second plunger part 1021. The second plunger part 1021 also includes a compartment (not labelled in the figure) for accommodating a first biasing member 104 with first and second ends 1040, 1041. The first and second ends 1040, 1041 of the first biasing member 104 engage with the rib 1007 and the baseplate 1030 respectively.

When the pair of fingers 1005 of the engaging member 1005 and stop ledge 1022 are not engaged, the first biasing element 104 is in a normal state, which means the first biasing element 104 is not compressed. And when the relative position of the plunger 102 and the barrel 100 changes (i.e., the plunger 102 is pushed inwardly into the barrel 100), the first biasing element 104 is compressed, since the first biasing element 104 is sandwiched between the rib 1007 and the baseplate 1030. The first biasing element 104 is implemented as a spring in the present invention. However, the first biasing element 104 is not limited to be implemented in certain form. Other elements or devices that are capable of exhibiting the characteristics of a spring can all be applied in the present invention.

Reference is again made to FIGS. 2a and 2b, the syringe 10 may connects with a puncturing apparatus 20. The puncturing apparatus 20 has a tip 201 detachably connected to an end of the outlet 1004 of the barrel 100. The puncturing apparatus 20 is implemented as a, but not limited to, a needle in the present invention. Moreover, the puncturing apparatus 20 includes a second inlet 202.

Figure 3:
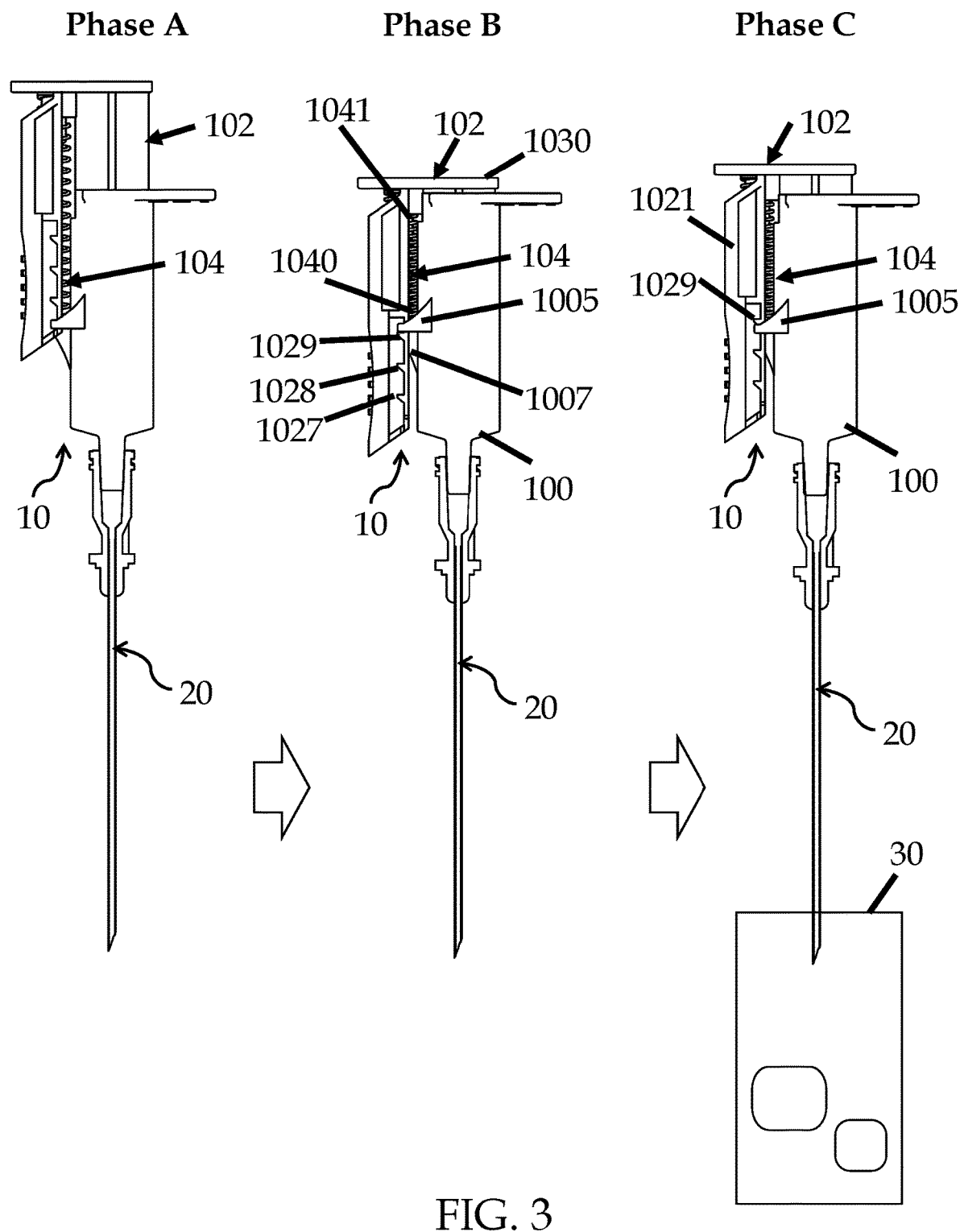
FIGS. 3 and 3b is schematic view illustrating the operation of the syringe according to an embodiment of the present invention.

How the syringe operate will be detailed in the following description. Reference is collectively made to FIG. 3 so that the description can be more comprehensive. FIG. 3 is schematic view illustrating the operation of the syringe according to an embodiment of the present invention. The syringe 10 of the present invention is suitable for medical staffs. Referring firstly to Phase A in FIG. 3a, the syringe 10 is in an original state, meaning no external force is applied to the syringe 10 (or in other words, no external force is applied to the plunger 102). In such state, the first biasing element 104 is also in the original state, meaning the first biasing element 104 neither being stretched nor compressed. In some other situations, the first biasing element 104 may be slightly compressed due to connections between device's (i.e., parts of the syringe) parts. However, whether the original state of the first biasing element 104 is free of compression or is slightly compressed by parts should not be limiting the scope of the present invention.

To be more specific, as shown in FIG. 2a, the second plunger part 1021 of the present embodiment has three stop ledges 1027, 1028, 1029. The three stop ledges, respectively is a first stop ledge 1027, a second stop ledge 1028 and a third stop ledge 1029. However, the number of stop ledges included in the second plunger part 1021 is not limited to three. The number may also be two, four or more than four. However, the second plunger part 1021 includes at least one stop ledge, so that the fingers 1005 of the engaging member of the barrel can engage with the stop ledge.

Reference is next made to the change from Phase A to Phase B in FIG. 3, when using the syringe 10, a user (not shown in the figure), for example, a doctor or a nurse should press the plunger 102 inwardly. The first biasing element 104 will be compressed accordingly. The user pushes the plunger 104 in a direction into the barrel 100 to make the fingers 1005 and the stop ledges 1027, 1028, 1029 to be engaged with each other. At this moment, since the two ends 1040, 1041 of the first biasing element 104 are respectively held by the rib 1007 and the baseplate 1030 of the plunger 102, the first biasing element 104 cannot be released. Further, in the present embodiment, the fingers 1005 engages with third stop ledge 1029, as shown in FIG. 3.

Since the fingers 1005 and the third stop ledge 1029 are engaged, the first biasing element 104 cannot force (or push) the plunger 102 to be drew back even if the first biasing element 104 now possesses a resilience to stretch back to its original state. Moreover, the pressure in the barrel 100 is the same as the pressure to the outside environment, since there's no such negative pressure created inside the barrel 100.

Further can be seen in the Phase B in FIG. 3 that the plunger 102 is pushed all the way down in the barrel 100, so that the first engaging element 1005 engages with the third stop ledge 1029. In some other embodiments, the fingers 1005 may engage with the second stop ledge 1028 or the first stop ledge 1027. It can be understood that which stop ledge the fingers 1005 engage is not limited. As long as the fingers 1005 engage with one of the stop ledges, the first biasing element 104 will all be compressed.

The syringe 10 is connected with the puncturing apparatus 20, as can be seen in FIGS. 2a-2b and 3. In the present invention, as described in the previous paragraph, the puncturing apparatus 20 is implemented as, but not limited to, a needle. The needle can be connected with the syringe 10 either before or after the fingers 1005 and the stop ledges 1027, 1028, 1029 are engaged. When the needle 20 is connected with the syringe 10 will not cause any pressure imbalance.

The user then thrust the syringe 10 connecting with the needle 20 into a living body. In the present embodiment, the living body is a human being. When the needle 20 enters into the flesh (or mass) 30, the user then makes the fingers 1005 and the stop ledges 1027, 1028, 1029 to be disengaged, as shown in the Phase C in the FIG. 3a. In the present embodiment, the user, by tapping, clicking or pressing the second plunger part 1021 towards the barrel 100 to make the fingers 1005 and the stop ledges 1027, 1028, 1029 to be disengaged. At this moment, since the needle 20 is in the flesh 30 of a human body, a negative pressure is created inside the reservoir 1001 (not show in the figure) of the barrel 100. Specifically, a restoring force generated by the first biasing element pushes the baseplate 1030 away from the proximal end 1002 of the barrel 100 when the fingers 1005 and the stop ledges 1027, 1028, 1029 are disengaged. Further, the piston 101 is moved in a direction to the proximal end 1002 of the barrel 100 (i.e., a volume of the reservoir is increasing), and then it decrease the pressure inside the reservoir (i.e., generating a negative pressure) according to Boyle-Mariotte law. The negative pressure will hold the first biasing element 104 to remain compressed. In other words, even the fingers 1005 and the stop ledges 1027, 1028, 1029 are no longer engaged with each other at this moment, the negative pressure will still prevent the first biasing element 104 from stretching back to its original length.

To be more specific regarding the Phase C in FIG. 3a, the fingers 1005 is now released from engaging with the third stop ledge 1029, but the plunger 102 will not be drawing back to the original position as shown in FIG. 3a due to the negative pressure. In such situation, the fingers 1005 is not engaging with any of the stop ledges 1027, 1028, 1029. The fingers 1005 is now in between the second and third stop ledges 1028, 1029. It can be understood that, the syringe 10 as shown in the Phase C in FIG. 3a is in an "aspiration" state.

In some situations, the first biasing element 104 may stretch a little after the fingers 1005 and the stop ledges 1027, 1028, 1029 are released from engagement, due to some imperfections to the devices, such as the connection between the needle 20 and the syringe 10 may not be fully sealed. However, the first biasing element 104 cannot reach to its fullest extent due to the negative pressure.

Figure 4:
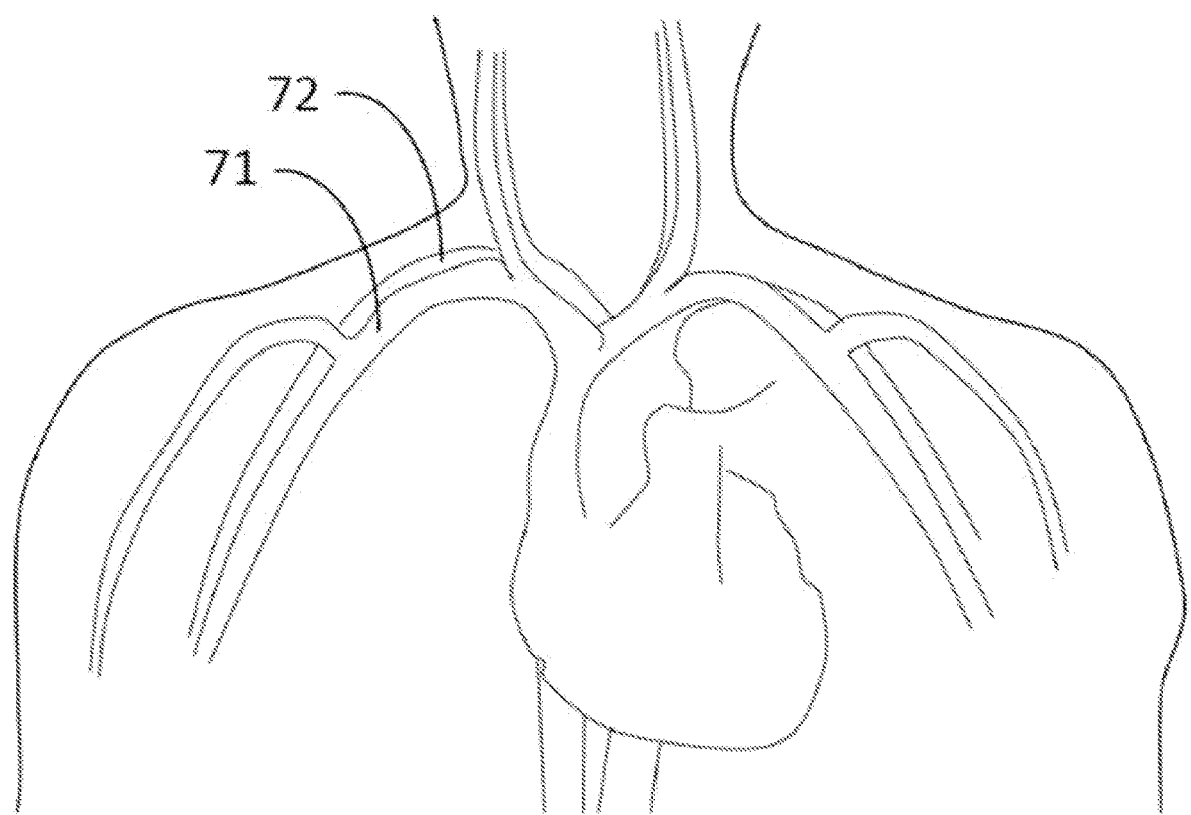
FIG. 4 shows an illustration of the veins and arteries of thorax, anterior view.

The user keeps pushing the syringe 10 inwardly into the flesh 30. The needle 20 moves in the flesh 30 when the user keeps pushing the syringe 10, however, the first biasing element 104 remains compressed during the movement, since the negative pressure remains and does not change or disappear. The negative pressure disappears when the second inlet 202 (i.e., the needle tip) of the needle 20 is moved into a space such as a vessel 40, as shown in FIG. 4. At this moment, the blood in the vessel 40 will flush into the barrel 100 through the needle 20. Since the negative pressure no longer exists and the blood pours into the barrel 100, the first biasing element 104 is released.

Figure 3B:
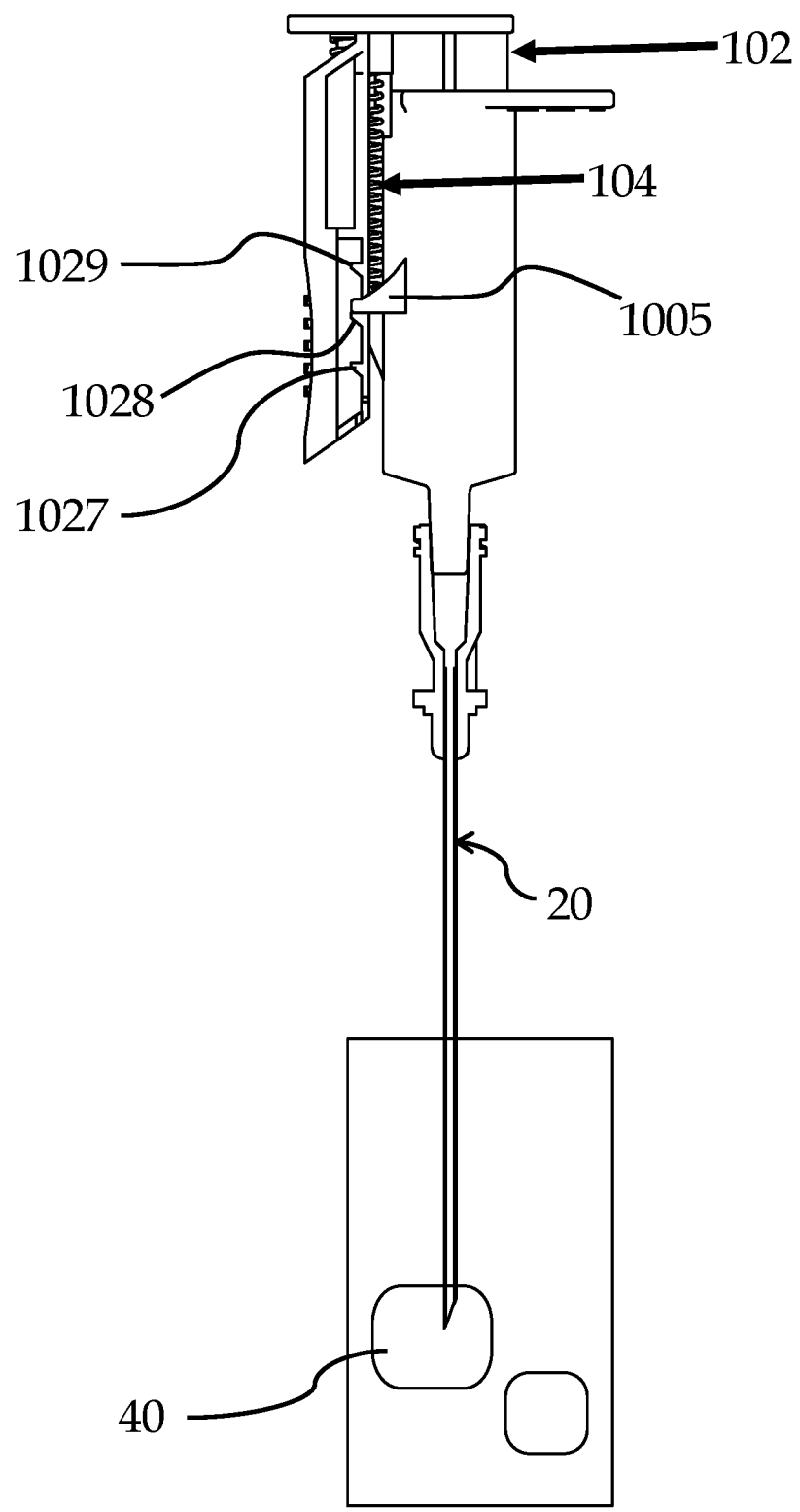

As can be seen in FIG. 3b, the first biasing element 104 now engages with the second stop ledge 1028. It can be understood that the fingers 1005 are released from engaging with the third stop ledge 1029 to be engaging with the second stop ledge 1028. In some other embodiment, the first biasing element 104 may be released to its original state, i.e., its original length. In such scenario, the fingers 1005 will not engage with any of the engaging portions 1027, 1028, 1029 (back to the Phase A as shown in FIG. 3a), so that the plunger 102 will be drawn back to its original position.

Some of the advantages of the present invention are listed below. One among is that the syringe 10 as provided in the present invention can be operated through one single hand. As can be seen in FIG. 1, the barrel 100 further includes a flange 1010. The flange 1010 provides users with a supporting point, so that user can easily push the plunger 102 into the barrel 100. That means a user can fully operate the syringe 10 with one single hand and spare the other hand for other tasks. From a doctor's, a nurse's or a medical staff's perspective, one spared hand can help the doctor or medical to perform other tasks during operation. In this regard, the syringe 10 brings conveniences to medical staff.

According to one of the embodiments of the present invention, the syringe as disclosed in the present invention is capable of distinguishing the vessel type. To be more specific, the syringe of the present invention is capable of assisting the operators to identify whether a vessel is a vein or an artery.

Before describing how the syringe is capable of identifying vessel type, reference is firstly made to FIG. 4, which shows an illustration of the veins and arteries of thorax, anterior view. For clarity, only main blood vessels are shown. The target vessel for central venous catheter (CVC) insertion is the subclavian vein 71. Because the subclavian artery 72 is close to the subclavian vein 71, the inadvertent arterial puncture rate with small needle ranges from 4.2% to 9.3%.

The syringe as provided is expected to further lower the inadvertent arterial puncture rate. However, though central venous access is used as an example to explain the advantages of the syringe of the present invention, the application of the syringe as provided herein is not restricted. The syringe as provided in the present invention is also suitable for other aspiration related applications, such as thoracentesis.

Figure 5A:
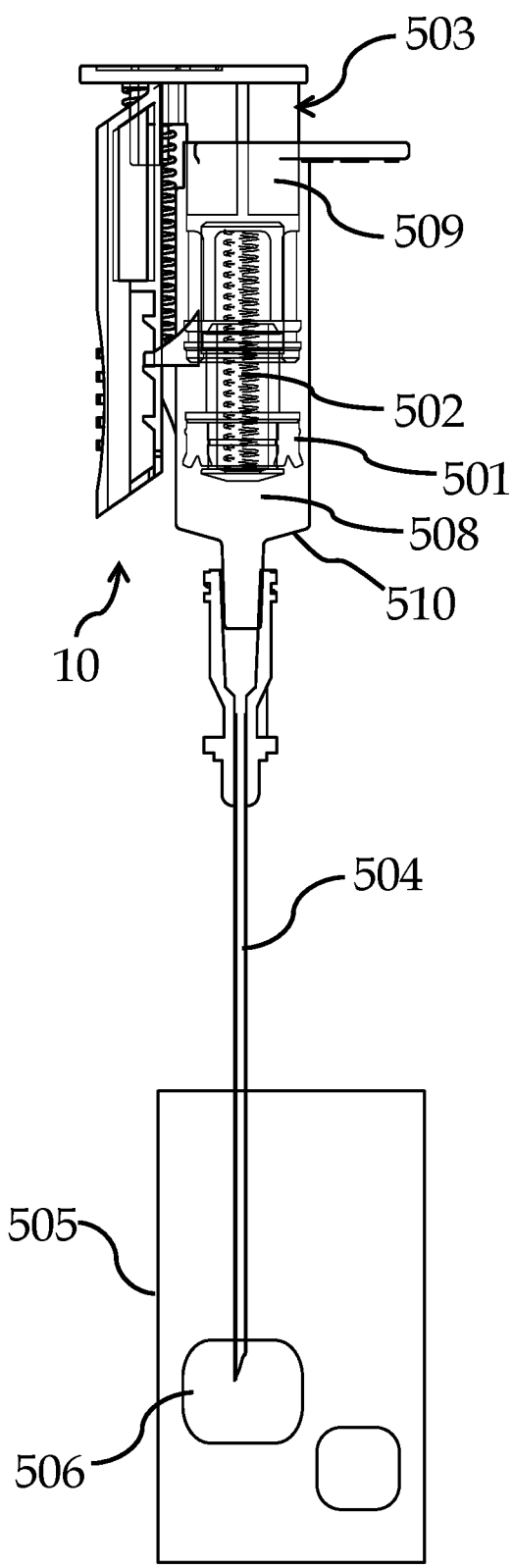
FIGS. 5a-5b are schematic view illustrating the operation of the syringe according to an embodiment of the present invention.
Figure 5B:
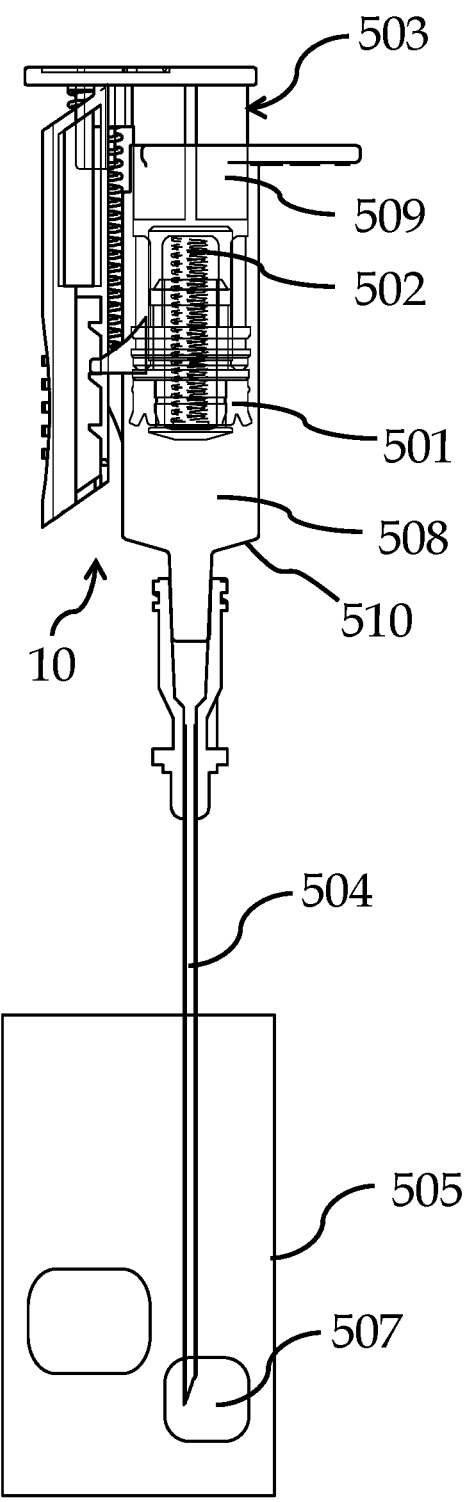

To achieve the goal of identifying a vessel type, referring collectively to FIGS. 5a and 5b. The piston 501 further includes a second biasing element 502 disposed between the piston 501 and the first plunger part 509. The operation of the syringe of the present embodiment is the same as those of the syringe in the previous, thus identical descriptions will be omitted for convenience, and only how this second biasing element 502 help to identify the vessel type will be delineated.

The plunger 503 is pressed, forcing the fingers and the stop ledge (either one among many stop ledges or one single ledge) to be engaged. The syringe 10 is connected with a needle 504, and the needle 504 thrust into a mess 505. The user clicks the plunger 503, releasing the engagement of the fingers and the stop ledge. The user pushes the syringe further into the mess 505. When the needle tip reaches to a vessel, blood flushes into the barrel (or into the reservoir 508).

If the needle tip reaches a vein 506, as shown in FIG. 5a, the blood pressure is relatively smaller than that of an artery. The blood pressure of the vein 506 cannot make the second biasing element 502 to be pressed. In other words, after the blood fully fills in the reservoir 508, the blood will not push and further to cause the second biasing element 502 to be compressed, since the relatively smaller blood pressure. If the needle tip reaches an artery 507, as shown in FIG. 5b, the blood will fully fills in the reservoir 508 as well, but since the blood pressure of the artery 507 is relatively larger than a vein, the blood pressure will further force the second biasing element 502 to be compressed.

The barrel 510 is preferable to be made of transparent material, such as transparent plastic. Since the barrel 510 can be seen through, one can identify if the piston 501 inside the barrel 510 moves (if the second biasing element 502 moves, it will drive the piston 501 to move accordingly). That is to say, users can identify, through observing whether the piston 501 moves, to determine whether the needle 504 reaches a vein 506 or an artery 507. If the needle tip of the needle 504 reaches a vein (e.g., the vein 506), the second biasing element 502 will not be forced to compress so that the piston 501 will not move, and if the needle tip of the needle 504 reaches an artery (e.g., the artery 507), the second biasing element 502 will be forced to compress so that the piston 501 will move accordingly.

The second biasing element 502 of the present embodiment is implement as, but not limited to, a spring. However, the implementation of the second biasing element 502 is not limited. Other materials or element that can reach the same effect of a spring can be implemented in the present invention.

In sum, since the barrel 510 is made of transparent material, the piston's change of position is visually detectable. By detecting whether the piston moves, what type of a vessel is can be thus identified by naked eyes. Thus, the syringe of the present invention brings conveniences for users to identify whether a needle connected with syringe is located at a correct position.

Figure 6A:
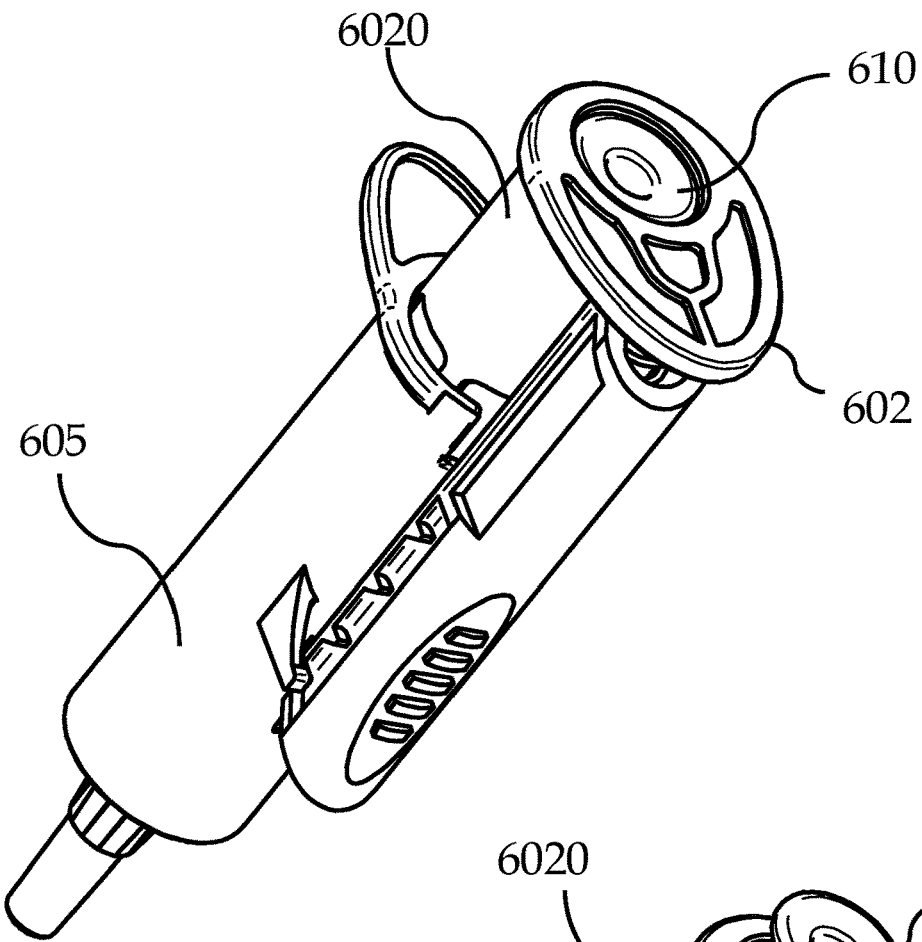
FIGS. 6a and 6b are schematic views illustrating a syringe according to one of the embodiments of the present invention.
Figure 6B:
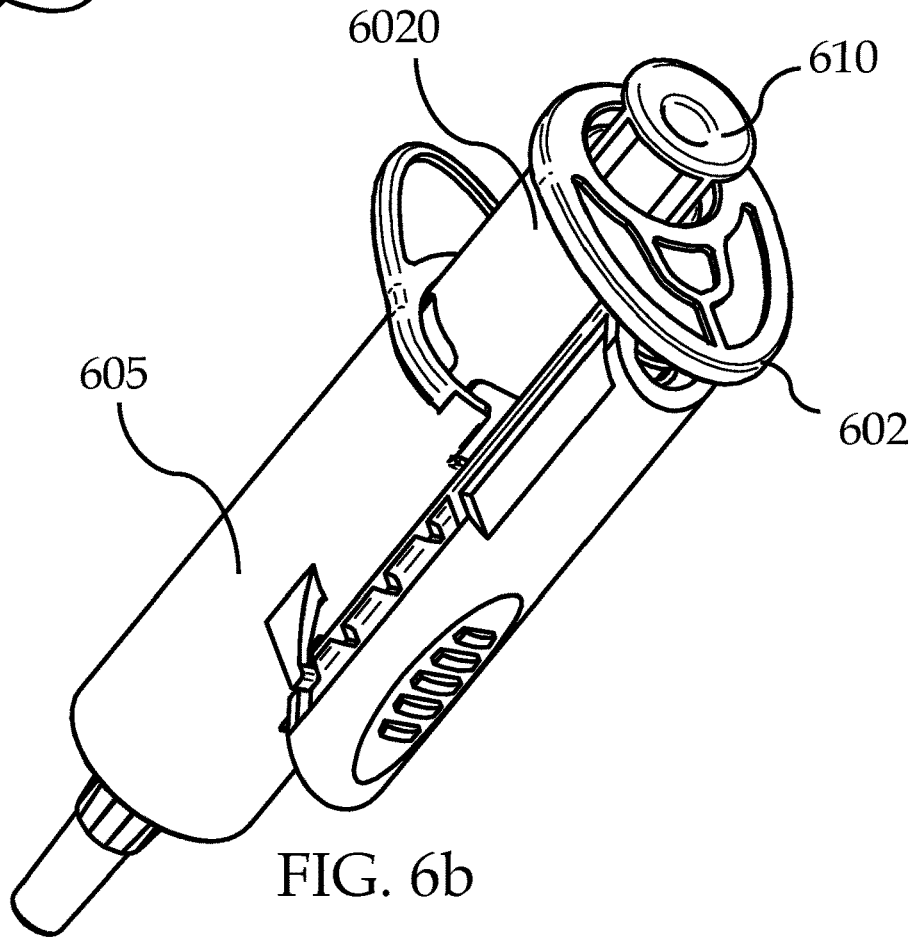

Reference is next made to FIGS. 6a and 6b, which illustrate a syringe according to one of the embodiments of the present invention. As can be seen in FIGS. 6a and 6b, the plunger 602 further includes an indicator 610. The indicator 610 passes through the first plunger part 6020. In the present embodiment, the indicator 610 solidly connects with the piston (not shown in FIGS. 6a and 6b). It can be further seen in FIG. 6a that the indicator 610 can be accommodated in the first plunger part 6020. Further, since the indicator 610 solidly connects with the piston, the indicator 610 will move accordingly if the piston moves.

Therefore, it can understood that, regarding the situation in which the needle tip reaches an artery and the blood pressure is great enough to force the second biasing element to be compressed, the indicator 610 will move with respect to the piston's movement. As shown in FIG. 6b, the indicator 610 is pushed out of the first plunger part 6020. This indicator 610 exhibits a much obvious identification that the needle tip is in an artery. For medical staffs, the indicator 610 provides a much clearer identification for them to assess whether the needle is in a vein or an artery.

Referring again to FIGS. 7a and 7b, the indicator 610 has an insertion hole 611 on a proximal end of the indicator 610. The insertion hole 611 provides a passage for a guidewire, such as a medical grade metal wire, to pass through. That is to say, when the syringe of the present invention is in used and is corrected positioned to a vein, the medical staff may next insert a guidewire through the insertion hole 611, the guidewire will pass all the way through the insertion hole 611, the first plunger part 6020, the barrel 605 and the needle 604 connected to the inlet of the syringe to the vein 701.

After placing the guidewire, the medical staff may draw the syringe away, leaving the guidewire connecting the vein.

FIGS. 7a and 7b provide a much more comprehensive illustration to the functionality of the indicator 610. Referring first to FIG. 7a, when the needle tips 601 reaches a vein 701, the blood pressure is unable to compress the second biasing element 703, thus the piston 704 will not move. When, in FIG. 7b, the needle tip reaches an artery 702, the blood pressure is big enough the force the second biasing element 703 to be compressed, and the piston 704 will move back, driving the indicator 610 to move back accordingly, so that the indicator 610 is moved out of the first part.

Reference is again made to FIGS. 6a, 6b, 7a and 7b, the indicator 610 may further includes a valve 707. When a guidewire is inserted into the insertion hole 611 and reaches to the vein, the valve 707 can prevent the blood from leaking out of the syringe. The valve 707 can also, prevent ambient air from flowing into the syringe when the pressure inside the barrel is negative. The valve 707 can further, prevent high pressure blood, such as artery blood, from leaking out from the syringe.

In one embodiment, the piston may further includes a pressure sensor (not shown in the figure). The pressure sensor may detect a pressure value in the barrel. Where the pressure sensor is placed (disposed) is not limited, as long as the pressure sensor can sense the pressure inside the barrel.

Figure 8A:
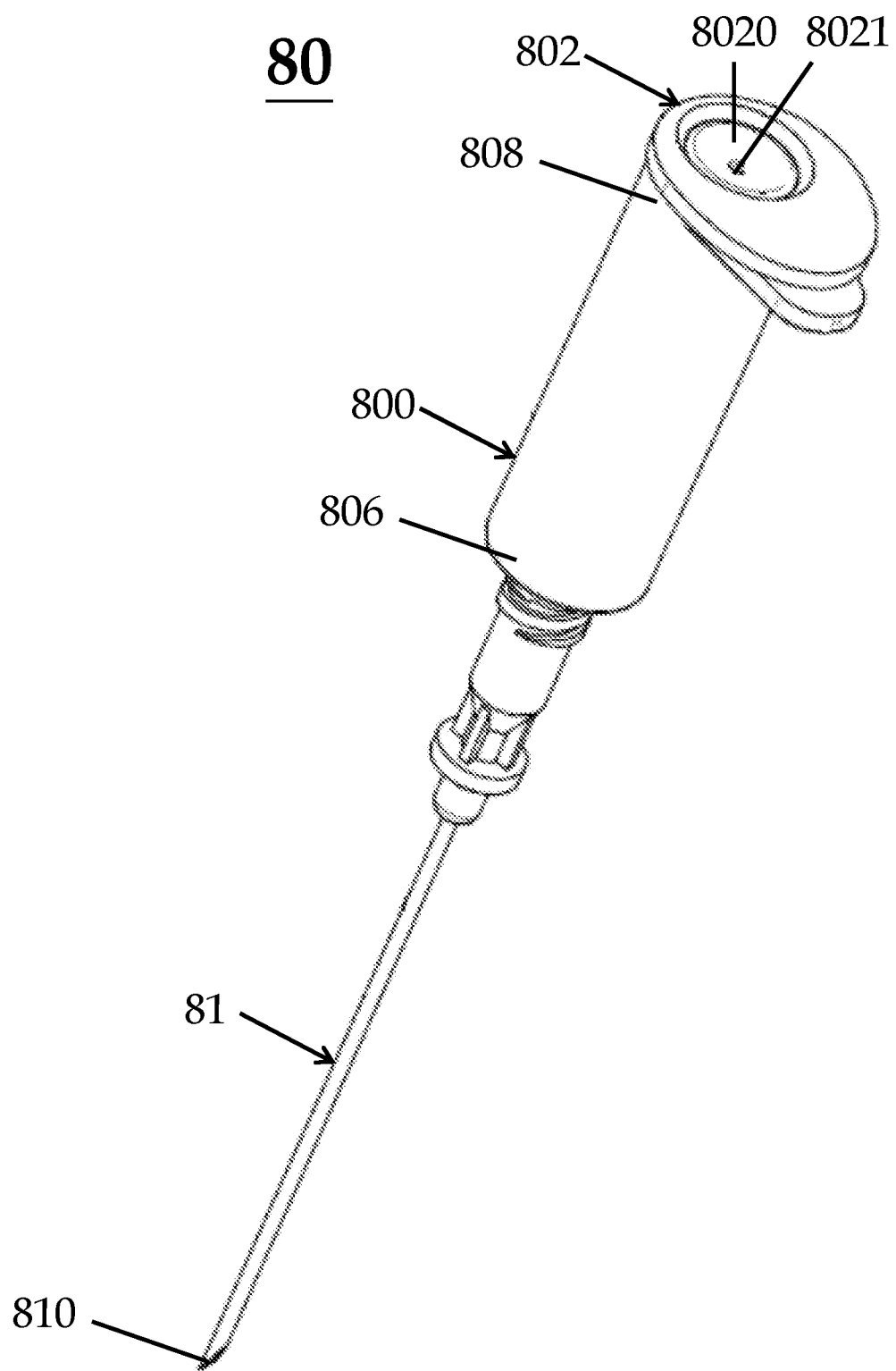

Reference is next made to FIGS. 8a-8c, which are schematic view illustrating a syringe according to one of the embodiments of the present invention. The syringe 80 includes a barrel 800, a piston 801, a plunger 802 and a biasing element 803. The barrel defines a reservoir 804 for receiving a constituent, and includes a proximal end 808 and a distal end 806 with an outlet 807. The piston 801 is movable within the reservoir 804, and the plunger 802 is movably within the reservoir 804 and slidably engages with the piston 801. The plunger 802 includes an indicator 8020 connecting with the piston 801. The indicator 8020 includes an inlet and an outlet deposited at a proximal and distal end 808, 806 respectively, a channel connecting the inlet and the outlet, and a valve. The biasing element 803 is disposed between the piston 801 and the plunger 802. A tensioning state of the biasing element 803 represents different relative position of the piston 801 in the reservoir 804 of the barrel 800.

The syringe 80 may connect with a puncturing apparatus 81. The puncturing apparatus 81 has a tip 810. The puncturing apparatus 81 is connected to the distal end 806 of the barrel 800. The operation of the syringe 80 will then be described in the following.

A user (not shown in the figure) first press the plunger 802, usually by his or her finger towards a direction into the barrel 800. The plunger 802 drives the piston 801 further into the barrel 800. The puncturing apparatus 81 of the present embodiment is implemented as a needle, and the first biasing element 803 is implemented as a spring.

After the needle 81 thrust into the mass 85, the user should be, pulling the plunger 802 slightly backward, in order to create a negative pressure inside the barrel 800. The user holds the plunger 802 to remain the negative pressure, and pushes the syringe 80 further into the mass.

As the user pushes further the syringe 80 into the mass 85, the needle 81 finally reaches a vessel (either a vein or an artery). When the needle tip 810 reaches a vessel, bloods flush into the barrel 800. If the needle 810 reaches a vein, the bloods will, as indicated above, flush into the barrel 800, but the piston 801 will not move, since the blood pressure is not big enough to force the biasing element 803 to be compressed. The biasing element 803, in some other situations, may be slightly compressed, due to different elastic modulus of different springs. Whether the biasing element 803 would be free from compression or be slightly compressed does not affect how the syringe 80 operate, and the scope of the present invention should not be limited.

If the needle 810 reaches an artery, due to the fact that the piston 801 and the indicator 8020 are physically connected (by medical glue or other means), meaning that when the piston 801 moves, the indicator 8020 will also move accordingly, the artery pressure will force the biasing element 803 to be compressed, since the blood pressure in an artery is relatively greater than that if a vein. Therefore, the bloods will force the piston 801 to move outwardly, the piston 801 drives the indicator 8020 at the same direction accordingly.

The indicator 8020 does not protrude from the end of the plunger 802 when the needle tip 810 is in the mass 85. The indicator 8020 will only protrudes out of the plunger 802 when the needle tip moves to a vessel. Therefore, by identifying the movement of the piston 801 and the indicator 8020, the user can easily identify that the needle 81 has reached a vessel. As described above, if the needle 81 reaches a vein, the indicator will be standstill, or be forced to move lightly (if the biasing element 803) is easier to be compressed. If the needle 81 reaches an artery, the indicator will move, and the movement is visually detectable. Therefore, users can easily identify whether the needle 81 reaches a vein or an artery. The barrel 800 may further includes a flange 811. The flange 811 provides user with convenience to hold the plunger 801.

Reference is further made back to FIG. 8a, the indicator 8020 may further includes an insertion hole 8021. The insertion hole 8021 provides a passage for a guidewire, such as a medical grade metal wire, to pass through. That is to say, when the syringe 80 of the present invention is in used and is corrected positioned to a vein, the user may next insert a guidewire through the insertion hole 8021 provides, the guidewire will pass all the way through the insertion hole 8021 provides, the barrel 800 and the needle 81 connected to the barrel 800 to the vessel. After placing the guidewire, the user may draw the syringe 80 away, leaving the guidewire connecting the vessel.

The barrel 800, preferably is made of transparent material, such as transparent plastic. Therefore, the piston 802 moving in the barrel 800 can be visually detected.

Figure 9:
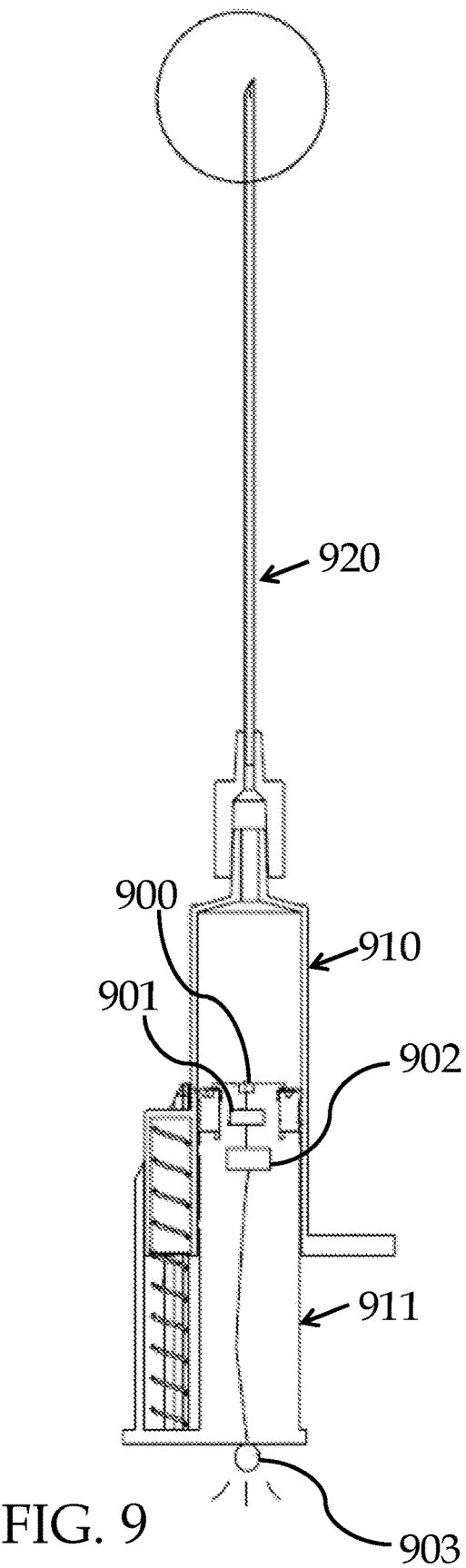
FIG. 9 is a schematic view illustrating a syringe according to one of the embodiments of the present invention.

Reference is then made to FIG. 9, which illustrates a syringe 90 according to one embodiments of the present invention. The present embodiment exemplifies a syringe with electronic pressure transducer. To be more specific, the syringe 90 includes a pressure indicating system 900. The pressure indicating system 900 includes a pressure sensor 901, a processing element 902 and an LED display unit 903. The pressure indicating system 900 may be encased in the barrel 910, or to be more specifically, in the plunger 911. The pressure sensor 901 is preferably an electronic pressure sensor, capable of sensing the pressure in the barrel 910.

The present embodiment as shown in FIG. 9 may also be used to distinguish a vein from an artery by confirming the pressure of a vessel. For example, if the needle 920 is in an artery, the LED display unit 903 will show a warning signal to warn the operator to avoid to insert the large-bore catheter inside this vessel and vice versa.

The invention claimed is:

1. A syringe for detecting pressure change, comprising;
a barrel defining a reservoir for receiving a constituent, including:
a proximal end and a distal end with an outlet;
an engaging member on an outer periphery of the barrel; and
a rib extending from the outer periphery of the barrel and disposed proximally to the engaging member;
a piston movable within the reservoir;
a plunger, including:
a first plunger part partially received by the reservoir and slidably engaged with the piston;
a second plunger part, including:
at least one stop ledge to which the engaging member releasably latch, and the stop ledge formed on a periphery of the second plunger part, and
a compartment for accommodating a first biasing member with first and second ends;
a baseplate supporting the first and second plunger parts, wherein the first and second ends of the first biasing member engage with the rib and the baseplate respectively,
wherein detecting the pressure change in a subject can be used to identify a target area in the subject.

2. The syringe for detecting pressure change as claim 1, wherein when the fingers of the engaging member and the at least one stop ledge are not engaged, the first biasing element is in a normal state, and when the relative position of the plunger and the barrel changes, the first biasing element is compressed.

3. The syringe for detecting pressure change as claim 1, wherein the first plunger part and the second plunger part are substantially in parallel.

4. The syringe for detecting pressure change as claim 1, wherein the first biasing element is a spring.

5. The syringe for detecting pressure change as claim 1, wherein the piston further includes a pressure sensor.

6. The syringe for detecting pressure change as claim 1, wherein the syringe further includes a puncturing apparatus having a tip, and the puncturing apparatus is detachably connected to the outlet end of the barrel.

7. The syringe for detecting pressure change as claim 6, wherein the puncturing apparatus further includes a second inlet.

8. The syringe for detecting pressure change as claim 1, wherein the piston further includes a second biasing element disposed between the piston and the first plunger part.

9. The syringe for detecting pressure change as claim 8, wherein the plunger further comprises an indicator connecting with the piston, and the indicator moves with respect to the piston's change of position.

10. The syringe for detecting pressure change as claim 9, wherein the indicator has an inlet and outlet deposited at a proximal end and distal end respectively, and a channel connecting the inlet and outlet.

11. The syringe for detecting pressure change as claim 9, wherein the indicator further comprises a valve.

12. A syringe for detecting pressure change, comprising;
a barrel defining a reservoir for receiving a constituent, including a proximal end and a distal end with an outlet;
a piston movable within the reservoir;
a plunger, including:
a first plunger part partially received by the reservoir, movably within the reservoir and slidably engaged with the piston;
a second plunger part, including:
at least one stop ledge to which the engaging member releasably latch, and the stop ledge formed on a periphery of the second plunger part, and a compartment for accommodating a first biasing element with first and second ends;

an indicator being configured to run through the piston and the first plunger part and slidably engaged with the first plunger part, including:

an inlet and outlet deposited at a proximal and distal end respectively;

a channel connecting the inlet and outlet; and a valve; and a second biasing element disposed between the piston and the first plunger part, wherein a tensioning state of the second biasing element represents a different relative position of the piston and the first plunger part, wherein detecting the pressure change in a subject can be used to identify a target area in the subject.

13. The syringe for detecting pressure change as claim 12, wherein the syringe further includes a puncturing apparatus having a tip detachably connected to the distal end of the barrel.

14. The syringe for detecting pressure change as claim 13, wherein the indicator is at a first position relative to the plunger when the second biasing element is at a first state, and the indicator maintains in the first position in response to a first pressure change inside the reservoir when the tip of the puncturing apparatus reaches a first location of a mass.

15. The syringe for detecting pressure change as claim 14, wherein the indicator does not protrude from an end of the first plunger part when the tip of the puncturing apparatus reaches the first location of a mass.

16. The syringe for detecting pressure change as claim 13, wherein the indicator is at a first position relative to the first plunger part when the biasing element is at a first state, and the indicator moves from the first position to a second position in response to a second state of the second biasing element resulting from a first pressure change inside the reservoir when the tip of the puncturing apparatus reaches a first location of a mass.

17. The syringe for detecting pressure change as claim 16, wherein, the indicator moves from the first position to a third position in response to a third state of the biasing element resulting from a second pressure change inside the reservoir when the tip of the puncturing apparatus reaches a second location of the mass, and the indicator's change of position is visually detectable.

18. The syringe for detecting pressure change as claim 17, wherein a portion of the indicator protrudes from an end of the first plunger part when the tip of the puncturing apparatus reaches the second location of the mass.

19. The syringe for detecting pressure change as claim 17, wherein the second pressure change is higher than the first pressure change.

20. A syringe for detecting pressure change, comprising;

a barrel defining a reservoir for receiving a constituent, including a proximal end and a distal end with an outlet;

a piston movable within the reservoir;

a plunger movably within the reservoir and slidably engaged with the piston, including:

an indicator being configured to run through the piston and the plunger and slidably engaged with the plunger, including:

an inlet and outlet deposited at a proximal and distal end respectively;

a channel connecting the inlet and outlet; and a valve; and a biasing element disposed between the piston and the plunger, wherein a tensioning state of the biasing element represents different relative position of the piston and the plunger, wherein detecting the pressure change in a subject can be used to identify a target area in the subject.

\* \* \* \* \*